United States Patent
Lu et al.

(10) Patent No.: US 10,676,495 B2
(45) Date of Patent: Jun. 9, 2020

(54) RHAMNOLIPID ESTERS AS NONIONIC SURFACTANTS FOR COSMETIC USE

(71) Applicant: Evonik Degussa GmbH, Essen (DE)

(72) Inventors: Xin Lu, Essen (DE); Sandra Nattland, Essen (DE); Monica Desiree van Logchem, Zevenberger (NL); Hans Henning Wenk, Mülheim an der Ruhr (DE); Fabien Cabirol, Paris (FR); Verena Dahl, Gladbach (DE); Ralph Scheuermann, Bottrop (DE); Kathrin Daniela Brandt, Düsseldorf (DE); Jochen Kleinen, Heinsbert (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/075,298

(22) PCT Filed: Feb. 15, 2017

(86) PCT No.: PCT/EP2017/053346
§ 371 (c)(1),
(2) Date: Aug. 3, 2018

(87) PCT Pub. No.: WO2017/144317
PCT Pub. Date: Aug. 31, 2017

(65) Prior Publication Data
US 2019/0256542 A1    Aug. 22, 2019

(30) Foreign Application Priority Data

Feb. 22, 2016 (EP) .................................. 16156654

(51) Int. Cl.
*C07H 15/06* (2006.01)
*A61Q 7/02* (2006.01)
*A61Q 9/02* (2006.01)
*C07H 1/00* (2006.01)
*A61K 8/60* (2006.01)

(52) U.S. Cl.
CPC .............. *C07H 15/06* (2013.01); *A61Q 7/02* (2013.01); *A61Q 9/02* (2013.01); *C07H 1/00* (2013.01); *A61K 8/604* (2013.01)

(58) Field of Classification Search
None
See application file for complete search history.

(56) References Cited

U.S. PATENT DOCUMENTS

| | | | |
|---|---|---|---|
| 9,243,212 B2 | 1/2016 | Kuppert et al. | |
| 9,434,755 B2 | 9/2016 | Schilling et al. | |
| 2014/0296168 A1 | 10/2014 | Schilling et al. | |
| 2017/0306264 A1 | 10/2017 | Peggau et al. | |
| 2017/0335238 A1 | 11/2017 | Schilling et al. | |
| 2018/0016525 A1 | 1/2018 | Scheuermann et al. | |
| 2018/0023040 A1 | 1/2018 | Schilling et al. | |

FOREIGN PATENT DOCUMENTS

| | | |
|---|---|---|
| EP | 2786742 A1 | 8/2014 |
| WO | 2017144317 A1 | 8/2017 |
| WO | 2017144318 A1 | 8/2017 |

OTHER PUBLICATIONS

Savelli et al. International Journal of Pharmaceutics (1999), vol. 182, pp. 221-236.*
Chayabutra et al. Biotechnol. Prog. (2001), vol. 17, pp. 419-423.*
Rebello, Sharrel, et al. "Surfactants: chemistry, toxicity and remediation." Pollutant Diseases, Remediation and Recycling. Springer, Cham, 2013. 277-320.*
"Alkyl." Merriam-Webster.com Dictionary, Merriam-Webster, https://www.merriam-webster.com/dictionary/alkyl. Accessed Apr. 3, 2020.*
Miao, S. et al; Ethylation of Di-rhamnolipids: A Green Route to Produce Novel Sugar Fatty Acid Nonionic Surfactants; J Surfact Deterg (Sep. 11, 2014) 17; pp. 1069-1080.
Westerduin P. et al; Synthesis of Methyl 3-[3-(2-0-cx-L-Rhamnopyranosyl-pt-L-Rham-Nopyranosyloxy) Decanoyloxy] Decanoate, A Rhamnolipid from Pseudomonas Aeruginosa; Carbohydrate Research, 180 (Sep. 15, 1988) pp. 195-205.

* cited by examiner

*Primary Examiner* — Patrick T Lewis
(74) *Attorney, Agent, or Firm* — Nexsen Pruet PLLC; Philip P. McCann

(57) ABSTRACT

The invention provides ester derivatives of rhamnolipids, formulations comprising these, and the use thereof.

20 Claims, No Drawings

RHAMNOLIPID ESTERS AS NONIONIC SURFACTANTS FOR COSMETIC USE

CROSS REFERENCE TO RELATED APPLICATIONS

This application is a 35 U.S.C. § 371 U.S. national phase entry of International Application No. PCT/EP2017/053346 having an international filing date of Feb. 15, 2017, which claims the benefit of European Application No. 16156654.2 filed Feb. 22, 2016, each of which is incorporated herein by reference in its entirety.

FIELD

The invention provides ester derivatives of rhamnolipids, formulations comprising these, and the use thereof.

BACKGROUND

Rhamnolipids are surfactants which can be prepared by means of fermentation. They are composed of one to two rhamnose units and one to three, mostly β-hydroxy fatty acids. The fatty acids can be saturated or unsaturated. The variation in the chain length and amount (congeners) of the fatty acid fractions has been described in a number of publications. (Howe et al., FEBS J. 2006; 273(22):5101-12; Abdel-Mawgoud et al., Appl Microbiol Biotechnol, 86, 2010; pp. 1323-1336). A few covalent derivatives of the fatty acid fractions of rhamnolipids are known. There are primarily a number of rhamnolipid esters described in the literature. Hirayama et al., FEBS Letters, Volume 139, Issue 1, 1982; Pages 81-85, describes the identification of rhamnolipid methyl esters in liquid cultures of *Pseudomonas aeruginosa*. Miao et al., Journal of Surfactants and Detergents, 17 (6), 2014; 1069-1080, describes the synthesis of di-rhamnolipid ethyl esters by the esterification with ethanol. Miao et al., European Journal of Lipid Science and Technology, 117, 2015; 156-160, describes the preparation of biopolyurethanes from di-rhamnolipid ethyl esters.

WO2001010447 and EP1889623 disclose the pharmaceutical and cosmetic applications of rhamnolipids and short-chain rhamnolipid esters (C1-C6; methyl to hexyl esters, linear or branched), especially for wound healing.

Moreover, Duynstee at al., European Journal of Organic Chemistry, 2, 1998; 303-307 and Bauer et al., Chem. Eur. J. 12, 2006; 7116-7124, describe the chemical synthesis of rhamnolipids; the intermediates synthesized herein are phenacyl esters and benzyl esters of rhamnolipids.

SUMMARY

It was an object of the invention to provide substances which bring about a soft skin feel after shaving that lasts for a long time.

DETAILED DESCRIPTION

Surprisingly, it has been found that the rhamnolipid esters described below are able to achieve the set object of the invention.

The present invention therefore provides rhamnolipid esters as described in Claim 1. The invention further provides a process for the preparation of the rhamnolipid esters according to the invention, and the use thereof.

One advantage of the present invention is that, following application of the formulations according to the invention, the smooth, silky-soft skin feel directly after shaving is retained for significantly longer than following application of non-inventive formulations.

Another advantage of the present invention is that following application of the formulations according to the invention the skin is less severely degreased.

A further advantage of the present invention is that the rhamnolipid esters according to the invention increase the mildness of formulations.

A yet further advantage of the present invention is that the formulations according to the invention can eliminate undesired odours from skin and at the same time leave behind a good skin feel.

A further advantage of the present invention is that the compositions according to the invention improve the skin elasticity.

A yet further advantage is that the preparation process is very mild and gentle, meaning that the desired sugar structure is not destroyed, but an esterification is nevertheless possible.

A further advantage is that the product can be isolated and worked up in an excellent manner.

The terms "rhamnolipid" and "rhamnolipid ester" in connection with the present invention also always include their corresponding salts.

The term "rhamnolipid ester" in connection with the present invention is understood as meaning compounds of the general formula (I),

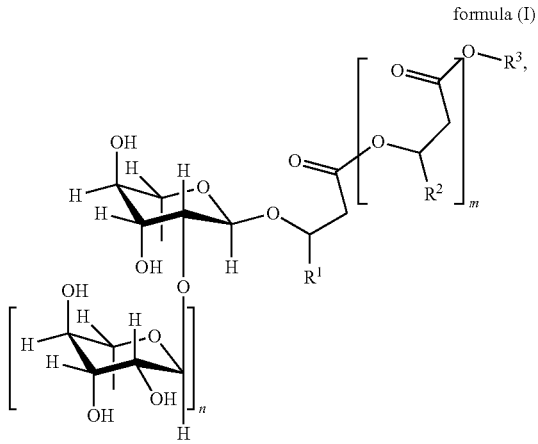

formula (I)

where m=2, 1 or 0, in particular 1 or 0, n=1 or 0, in particular 1, $R^1$=organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12, $R^2$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12, and $R^3$=aliphatic radical with 1 to 32 carbon atoms, preferably 7 to 32 carbon atoms, particularly preferably 8 to 24 carbon atoms, especially particularly preferably 10 to 18 carbon atoms.

The term "mono-rhamnolipid" in connection with the present invention is understood as meaning compounds of the general formula (I) where $R^3$=H or salts thereof, in which n=0.

Distinct rhamnolipids are abbreviated according to the following nomenclature:

"diRL-CXCY" is understood as meaning di-rhamnolipids of the general formula (I) where $R^3$=H or salts thereof, in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

"monoRL-CXCY" is understood as meaning mono-rhamnolipids of the general formula (I) where $R^3$=H or salts thereof, in which one of the radicals $R^1$ and $R^2$=$(CH_2)_o$—$CH_3$ where o=X-4 and the remaining radical $R^1$ or $R^2$=$(CH_2)_o$—$CH_3$ where o=Y-4.

The nomenclature used therefore does not differ between "CXCY" and "CYCX".

For rhamnolipids where m=0, monoRL-CX or diRL-CX is used accordingly.

If one of the abovementioned indices X and/or Y is provided with ":Z", this signifies that the respective radical $R^1$ and/or $R^2$=an unbranched, unsubstituted hydrocarbon radical having X-3 or Y-3 carbon atoms having Z double bonds.

Analogous nomenclature is used for rhamnolipid esters in the form di/monoRL-CXCY:Z esters.

The "pH" in connection with the present invention is defined as the value which is measured for the corresponding substance at 25° C. after stirring for 5 minutes using a pH electrode calibrated in accordance with ISO 4319 (1977).

Unless stated otherwise, all percentages (%) given are percentages by mass.

The present invention provides Rhamnolipid esters of the general formula (I)

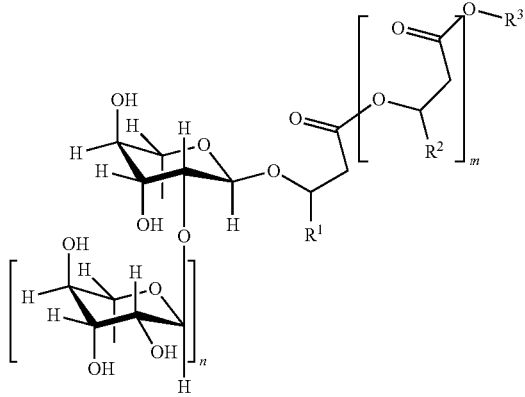

formula (I)

where
m=2, 1 or 0, in particular 1 or 0,
n=1 or 0, in particular 1,
$R^1$=organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably those selected from the group consisting of pentenyl, heptenyl, nonenyl, undecenyl and tridecenyl and $(CH_2)_o$—$CH_3$ where o=1 to 23, preferably 4 to 12,
$R^2$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably those selected from the group consisting of pentenyl, heptenyl, nonenyl, undecenyl and tridecenyl and $(CH_2)_o$—$CH_3$ where o=1 to 23, preferably 4 to 12, and
$R^3$=aliphatic radical having 7 to 32 carbon atoms, preferably 8 to 24 carbon atoms, particularly preferably 10 to 18 carbon atoms.

Particularly preferred rhamnolipid esters according to the invention are selected from diRLC10C10 esters, diC8C10 esters, diRLC10C12 esters, diRLC10C12:1 esters and monoRLC10C10 esters where $R^3$=aliphatic radical having 7 to 32 carbon atoms, preferably 8 to 24 carbon atoms, particularly preferably 10 to 18 carbon atoms.

Likewise particularly preferred rhamnolipid esters according to the invention are characterized in that $R^3$ is selected from the group of the radicals $R^3$ derived from $OHR^3$=natural fatty alcohol. In this connection, in particular rhamnolipid esters are according to the invention preferably selected from diRLC10C10 esters, diC8C10 esters, diRLC10C12 esters, diRLC10C12:1 esters and monoRLC10C10 esters. The term "natural fatty alcohol" in connection with the present invention is understood to mean the alcohols which may be obtained by reduction of natural triacylglycerols, fatty acids or fatty acid methyl esters; these comprise in particular linear, saturated or unsaturated primary alkan-1-ols having 8-32 carbon atoms.

Very particularly preferred rhamnolipid esters according to the invention are characterized in that $R^3$ is selected from branched or linear alkyl radicals, preferably having 8 to 22, in particular 12 to 18, carbon atoms. In this connection, in particular rhamnolipid esters are preferably selected from diRLC10C10 esters, diC8C10 esters, diRLC10C12 esters, diRLC10C12:1 esters and monoRLC10C10 esters.

Very particularly preferred rhamnolipid esters according to the invention are characterized in that $R^3$ is selected from the group comprising, preferably consisting of, lauryl, myristyl, palmityl and stearyl radicals. In this connection, in particular rhamnolipid esters are according to the invention preferably selected from diRLC10C10 esters, diC8C10 esters, diRLC10C12 esters, diRLC10C12:1 esters and monoRLC10C10 esters.

The rhamnolipid esters according to the invention are preferably mixture compositions of rhamnolipid esters which are characterized in particular in that they contain mono- and di-rhamnolipid esters.

Depending on the application, it may be preferred that the mixture compositions according to the invention comprise more percent by weight of mono-rhamnolipid esters than di-rhamnolipid esters or more percent by weight of di-rhamnolipid esters than mono-rhamnolipid esters, where the percentages by weight refer to all of the mono- and di-rhamnolipid esters present in the mixture composition.

Thus, for example, the mixture compositions according to the invention can comprise, for example, more than 60% by weight, in particular more than 80% by weight, or even more than 95% by weight, of di-rhamnolipid esters, or else also for example more than 60% by weight, in particular more than 80% by weight, or even more than 95% by weight, of mono-rhamnolipid esters, where the percentages by weight refer to all of the mono- and di-rhamnolipid esters present in the mixture composition.

The present invention further provides a process for the preparation of rhamnolipid esters comprising the process steps A) provision of at least one rhamnolipid, B) reaction of the rhamnolipid with at least one coupling reagent, C) reaction of the rhamnolipid activated by process step B) with an alcohol having 1 to 32, especially 3 to 32, carbon atoms, and optionally D) purification of the rhamnolipid ester.

Process step A) is carried out according to the generally known processes of the prior art, in particular using genetically modified microorganisms which preferably overexpress rhamnolipid synthesis genes, these genes preferably being selected from rhlA, rhlB and rhlC. Corresponding instructions can be found by the person skilled in the art in e.g. US2014296168 and WO2012013554.

It is preferred according to the invention that in process step B) the coupling reagent used is at least one selected from the group comprising, preferably consisting of, dicyclohexylcarbodiimide, diisopropylcarbodiimide, 1-(3-dimethylaminopropyl)-3-ethylcarbodiimide hydrochloride, N-cyclohexyl-N'-(2'-morpholinoethyl)carbodiimide metho-p-toluenesulphonate, N-benzyl-N'-3' dimethylaminopropyl-carbodiimide hydrochloride, 1-ethyl-3-(3-dimethylaminopropyl)carbodiimide, N-ethylcarbodiimide hydrochloride and carbonyldiimidazole, particularly preferably dicyclohexylcarbodiimide and diisopropylcarbodiimide.

Likewise, it is preferred according to the invention that in process step C) at least one catalyst selected from the group comprising, preferably consisting of, N-ethyldiisopropylamine, trialkylamines, pyridine, 4-dimethylaminopyridine and hydroxybenzotriazole, in particular hydroxybenzotriazole, is used.

Processes preferred according to the invention preferably lead to rhamnolipid esters of the general formula (I), formula (I)

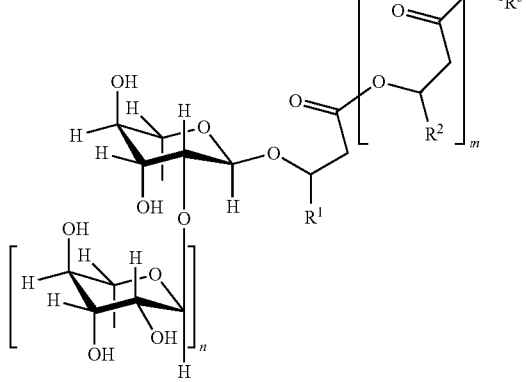

where m=2, 1 or 0, in particular 1 or 0, n=1 or 0, in particular 1, $R^1$=organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably those selected from the group consisting of pentenyl, heptenyl, nonenyl, undecenyl and tridecenyl and $(CH_2)_o$—$CH_3$ where o=1 to 23, preferably 4 to 12, $R^2$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably those selected from the group consisting of pentenyl, heptenyl, nonenyl, undecenyl and tridecenyl and $(CH_2)_o$—$CH_3$ where o=1 to 23, preferably 4 to 12, and $R^3$=aliphatic radical having 3 to 32 carbon atoms, preferably 7 to 32 carbon atoms, particularly preferably 8 to 24 carbon atoms, especially particularly preferably 10 to 18 carbon atoms, and also particularly preferably rhamnolipid esters designated above as particularly preferred according to the invention.

Thus, for example preferably in process step A) preferably rhamnolipids selected from diRLC10C10, diC8C10, diRLC10C12, diRLC10C12:1 and monoRLC10C10 or mixtures thereof are used. Accordingly preferred is the use of alcohols in process step C) selected from the group of the aliphatic alcohols having 7 to 32 carbon atoms and fatty alcohols.

The invention further provides the rhamnolipid esters obtainable by the process according to the invention, in particular those which are obtainable through the use of alcohols in process step C) selected from the group of the aliphatic alcohols having 7 to 32 carbon atoms and fatty alcohols.

The rhamnolipid esters according to the invention can advantageously be incorporated into in particular cosmetic formulations, preferably for shaving applications.

Consequently, the present invention further provides the use of the rhamnolipid esters according to the invention for producing formulations, in particular cosmetic formulations, and the formulations themselves, in particular cosmetic formulations, preferably for shaving applications, which comprise the rhamnolipid esters according to the invention.

The formulations according to the invention are preferably aqueous formulations.

The term "aqueous formulation" in connection with the present invention is to be understood as meaning a formulation which comprises at least 5% by weight of water, based on the overall composition under consideration.

According to the invention, it is preferred if the formulations according to the invention comprise the rhamnolipid esters according to the invention in an amount of from 0.05% by weight to 40% by weight, preferably from 0.2% by weight to 20% by weight, particularly preferably from 0.5% by weight to 12% by weight, where the percentages by weight refer to the total formulation.

Preferred formulations according to the invention comprise, in addition to the rhamnolipid esters according to the invention, at least one further surfactant, it being possible to use, for example, anionic, nonionic, cationic and/or amphoteric surfactants. From an applications point of view, preference is given to mixtures of anionic and nonionic surfactants. The total surfactant content of the aqueous formulation is preferably 5 to 60% by weight and particularly preferably 15 to 40% by weight, based on the total formulation.

The nonionic surfactants used are preferably alkoxylated, advantageously ethoxylated, in particular primary alcohols having preferably 8 to 18 carbon atoms and on average 1 to 12 mol of ethylene oxide (EO) per mole of alcohol, in which the alcohol radical can be linear or preferably 2-methyl-branched or can comprise linear and methyl-branched radicals in a mixture, as are usually present in oxo alcohol radicals. Of particular preference, however, are alcohol ethoxylates with linear radicals from alcohols of native origin having 12 to 18 carbon atoms, for example from coconut, palm, tallow fatty or oleyl alcohol, and on average 2 to 8 EO per mole of alcohol. The preferred ethoxylated alcohols include for example C12-C14-alcohols having 3 EO, 4 EO or 7 EO, C9-C11-alcohol with 7 EO, C13-C15-alcohols with 3 EO, 5 EO, 7 EO or 8 EO, C12-C18-alcohols with 3 EO, 5 EO or 7 EO and mixtures of these, such as mixtures of C12-C14-alcohol with 3 EO and C12-C18-alcohol with 7 EO. The stated degrees of ethoxylation are statistical average values which can be an integer or a fraction for a specific product. Preferred alcohol ethoxylates have a narrowed homologue distribution. In addition to these nonionic surfactants, it is also possible to use fatty alcohols with more than 12 EO. Examples thereof are tallow fatty alcohol with 14 EO, 25 EO, 30 EO or 40 EO. It is also possible to use nonionic surfactants which contain EO and PO (propylene oxide) groups together in the molecule. Here, it is possible to use block copolymers with EO-PO block units or PO-EO block units, but also EO-PO-EO copolymers or PO-EO-PO copolymers.

It is of course also possible to use mixed alkoxylated nonionic surfactants in which EO and PO units are not distributed blockwise, but randomly. Such products are obtainable through the simultaneous action of ethylene oxide and propylene oxide on fatty alcohols.

Moreover, further nonionic surfactants that can be used are also alkyl glycosides.

A further class of preferably used nonionic surfactants, which are used either as the sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters, as are described, for example, in the Japanese patent application JP 58/217598 or which are prepared preferably by the process described in the international patent application WO-A-90/13533.

Also nonionic surfactants of the amine oxide type, for example N-cocoalkyl-N,N-dimethylamine oxide and N-tallow-alkyl-N,N-dihydroxyethylamine oxide, and of the fatty acid alkanolamide type can be suitable. The amount of these nonionic surfactants is preferably not more than that of the ethoxylated fatty alcohols, in particular not more than half thereof.

Further suitable surfactants are polyhydroxy fatty acid amides; polyhydroxy fatty acid amides are substances which can usually be obtained by reductive amination of a reducing sugar with ammonia, an alkylamine or an alkanolamine and subsequent acylation with a fatty acid, a fatty acid alkyl ester or a fatty acid chloride.

Anionic surfactants that can be used are for example those of the sulphonate and sulphate types. Suitable surfactants of the sulphonate type here are preferably C9-C13-alkylbenzenesulphonates, olefinsulphonates, i.e. mixtures of alkene- and hydroxyalkanesulphonates and disulphonates, as are obtained for example from C12-C18-monoolefins with terminal or internal double bond by sulphonation with gaseous sulphur trioxide and subsequent alkaline or acidic hydrolysis of the sulphonation products. Also of suitability are alkanesulphonates, which are obtained from C12-C18-alkanes for example by sulphochlorination or sulphoxidation with subsequent hydrolysis or neutralization. Likewise of suitability are also the esters of α-sulpho fatty acids (ester sulphonates), for example the α-sulphonated methyl esters of the hydrogenated coconut, palm kernel or tallow fatty acids.

Further suitable anionic surfactants are sulphated fatty acid glycerol esters. Fatty acid glycerol esters are to be understood as meaning the mono-, di- and triesters and mixtures thereof, as are obtained during the production by esterification of a monoglycerol with 1 to 3 mol of fatty acid or during the transesterification of triglycerides with 0.3 to 2 mol of glycerol. Preferred sulphated fatty acid glycerol esters here are the sulphation products of saturated fatty acids having 6 to 22 carbon atoms, for example of caproic acid, caprylic acid, capric acid, myristic acid, lauric acid, palmitic acid, stearic acid or behenic acid.

Preferred alk(en)yl sulphates are the alkali metal and in particular the sodium salts of the sulphuric acid half-esters of the C12-C18-fatty alcohols, for example from coconut fatty alcohol, tallow fatty alcohol, lauryl, myristyl, cetyl or stearyl alcohol or the C10-C20 oxo alcohols and those half-esters of secondary alcohols of these chain lengths. Furthermore, preference is given to alk(en)yl sulphates of the stated chain length which contain a synthetic straight-chain alkyl radical produced on a petrochemical basis which have an analogous degradation behaviour to the equivalent compounds based on fatty chemical raw materials. From a washing point of view, preference is given to the C12-C16-alkyl sulphates and C12-C18-alkyl sulphates and C14-C18-alkyl sulphates. Also 2,3-alkyl sulphates, which are prepared for example according to the U.S. Pat. No. 3,234,258 or 5,075,041 and can be obtained as commercial products of the Shell Oil Company under the name DAN®, are suitable anionic surfactants.

Also the sulphuric acid monoesters of the straight-chain or branched C7-C20-alcohols ethoxylated with 1 to 6 mol of ethylene oxide, such as 2-methyl-branched C9-C11-alcohols with on average 3.5 mol of ethylene oxide (EO) or C12-C18-fatty alcohols with 1 to 4 EO, are suitable. On account of their high foaming behaviour, they are used in cleaners only in relatively small amounts, for example in amounts of from 1 to 5% by weight.

Further suitable anionic surfactants are also the salts of alkylsulphosuccinic acid, which are also referred to as sulphosuccinates or as sulphosuccinic acid esters and which are monoesters and/or diesters of sulphosuccinic acid with alcohols, preferably fatty alcohols and in particular ethoxylated fatty alcohols. Preferred sulphosuccinates contain C8-C18 fatty alcohol radicals or mixtures thereof. Particularly preferred sulphosuccinates contain a fatty alcohol radical which is derived from ethoxylated fatty alcohols. In this case, sulphosuccinates whose fatty alcohol radicals are derived from ethoxylated fatty alcohols with a narrow homologue distribution are in turn particularly preferred. Likewise, it is also possible to use alk(en)ylsuccinic acid having preferably 8 to 18 carbon atoms in the alk(en)yl chain or salts thereof.

Particularly preferred anionic surfactants are soaps. Saturated and unsaturated fatty acid soaps, such as the salts of lauric acid, myristic acid, palmitic acid, stearic acid, (hydrogenated) erucic acid and behenic acid and in particular soap mixtures derived from natural fatty acids, for example coconut, palm kernel, olive oil or tallow fatty acids.

The anionic surfactants including the soaps can be present in the form of their sodium, potassium or ammonium salts as well as soluble salts of organic bases, such as mono-, di- or triethanolamine. Preferably, the anionic surfactants are present in the form of their sodium or potassium salts, in particular in the form of the sodium salts.

Amphoteric surfactants that can be used according to the invention are those surface-active compounds which carry in the molecule at least one quaternary ammonium group and at least one —COO⁻ or —SO₃⁻ group. Particularly preferred amphoteric surfactants in this connection are betaine surfactants such as alkyl- or alkylamidopropylbetaines. In particular, betaines such as the N-alkyl-N,N-dimethylammonium glycinates, e.g. cocoalkyldimethylammonium glycinate, N-acylaminopropyl-N,N-dimethylammonium glycinates, e.g. cocoacylaminopropyldimethylammonium glycinate, C12-C18-alkyldimethylacetobetaine, cocoamidopropyldimethylacetobetaine, 2-alkyl-3-carboxymethyl-3-hydroxyethylimidazolines and sulphobetaines having in each case 8 to 18 carbon atoms in the alkyl or acyl group, and cocoacylaminoethyl hydroxyethyl carboxymethylglycinate are preferred here. A particularly preferred zwitterionic surfactant is the N,N-dimethyl-N-(lauroylamidopropyl)ammonium acetobetaine known under the INCI name Cocamidopropyl Betaine.

Further suitable amphoteric surfactants are the group of amphoacetates and amphodiacetates, in particular for example coco- or laurylamphoacetates or -diacetates, the group of the amphopropionates and amphodipropionates and the group of the amino acid-based surfactants such as acyl glutamates, in particular Disodium Cocoyl Glutamate and Sodium Cocoyl Glutamate, acyl glycinates, in particular Cocoyl Glycinate, and acyl sarcosinates, in particular Ammonium Lauroyl Sarcosinate and Sodium Cocoyl Sarcosinate.

The formulations according to the invention particularly preferably comprise a fragrance.

The formulations according to the invention can further comprise at least one additional component selected from the group of
  emollients,
  emulsifiers,
  thickeners/viscosity regulators/stabilizers,
  UV light protection filters,
  antioxidants,
  hydrotropes (or polyols),
  solids and fillers,
  film formers,
  pearlescence additives,
  deodorant and antiperspirant active ingredients,
  insect repellents,
  self-tanning agents,
  preservatives,
  conditioners,
  dyes,
  cosmetic active ingredients,
  care additives,
  superfatting agents,
  solvents.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts used of these components, reference is made expressly to the relevant handbooks known to the person skilled in the art, for example K. Schrader, "Grundlagen und Rezepturen der Kosmetika [Fundamentals and principles of cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

The rhamnolipid esters according to the invention and the formulations according to the invention comprising the rhamnolipid esters according to the invention can be used advantageously for preparing a surface for shaving.

The present invention further provides the cosmetic use of the rhamnolipid esters according to the invention and/or of the formulations according to the invention in shaving applications.

The present invention further provides the cosmetic use of the rhamnolipid esters according to the invention and/or of the formulations according to the invention for inhibiting hair growth.

The examples listed below describe the present invention by way of example, without any intention of restricting the invention, the scope of application of which is apparent from the entirety of the description and the claims, to the embodiments specified in the examples.

EXAMPLES

Example 1: Preparation of Di-Rhamnolipids

A fermentation with a recombinant strain *Pseudomonas putida* KT2440S pBBRIMCS2-Plac-rhlABC-T-Ptac-rhlC-T was carried out. The construction of the strain is described in US2014296168. The preculture in the shake flask was carried out as described in WO2012013554. For the main culture, a mineral medium (M9) was likewise used. The fermentation takes place in a glucose-limited fed-batch process in a 2 litre fermenter. The feeding in of glucose is regulated by reference to the dissolved-oxygen signal. The oxygen partial pressure of the fermentation broth was regulated at 20% saturation via the stirrer speed. The pH is regulated to 7 via a pH electrode and addition of 2M sulphuric acid or of a 20% by weight ammonia solution. In order to prevent excessive foaming of the fermentation broth, the antifoam DOW Corning 1500 was metered in as required. The fermentation was conducted over 4 days to a dry biomass of 15 g/l. The rhamnolipid concentration was determined by HPLC and was 9.8 g/l. After separating off the cells by means of centrifugation at 10 000 g, the fermentation broth was adjusted to a pH of 3.1 by adding concentrated $H_2SO_4$. Renewed centrifugation gave a pasty solid concentrate with an RL fraction of 45% by weight and with a viscosity of >10 000 mPas. With continuous stirring, a 50% strength by weight aqueous KOH solution was added to the pasty suspension of the concentrated rhamnolipid precipitate and a pH of 6 was established. The pasty mass liquefied at this point with an accompanying sharp drop in viscosity. The suspension gave rise to a clear solution. By adding water, the solution was adjusted to an active content of 35% by weight. The rhamnolipid purity was >90% by weight, based on the dry mass.

Rhamnolipid species verified by HPLC were:

| | |
|---|---|
| RL total [%] (HPLC) | 91 |
| diRL-C8C10 | 13.9 |
| monoRL-C8C10 | 0.51 |
| diRL-C10C10 | 61.4 |
| monoRL -C10C10 | 1.4 |
| diRL-C10C12:1 | 5.9 |
| diRL-C10C12 | 5.5 |
| other RL | 2.2 |

Example 2: Preparation of Mono-Rhamnolipids

The 35% by weight rhamnolipid solution prepared as described above was diluted to 1% by adding water. Two litres of this solution were heated to 50° C. With gentle stirring, 200 units of a thermostable rhamnosidase (ThermoActive™ Rhamnosidase A, Prokazyme) were added and the reaction was carried out overnight. After 20 h, a sample of the solution was analysed by means of HPLC. The di-rhamnolipid had been completely converted to mono-rhamnolipid and rhamnose. Then, the enzyme was deactivated for one hour at 80° C. The entire mixture was then freeze-dried. The freeze-dried product was adjusted to a mono-rhamnolipid active content of 35% by weight by adding water.

Example 3: Synthesis of Di-Rhamnolipid Lauryl Ester

To activate the acid function, 25 g of di-rhamnolipid from Example 1 with 6.25 ml of diisopropylcarbodiimide were dissolved in THF at 55° C. If the mixture achieves an acid number of <2, 6.5 g of dodecyl alcohol are added, as is 1% by weight of 4-dimethylaminopyridine for the catalysis. Any unreacted coupling reagent should be deactivated beforehand by adding 2 ml of water. After a reaction time of 10 h, work-up is carried out. The reaction mixture is dried on a rotary evaporator (45° C., <300 mbar); purification takes place by extracting through shaking with ethyl acetate (1):water (1) in two steps with 250 ml in each case. The rhamnolipid ester remains in the ethyl acetate phase. This is likewise dried on a rotary evaporator (45° C., <100 mbar), the viscous rhamnolipid ester remains.

Further purification of the product can take place by means of column chromatography. For this, Silica 60 Gel (SIGMA Aldrich) serves as stationary phase and ethyl acetate (99):water (1) with 1% acetic acid serves as mobile phase. Polar by-products or possible cleavage products are removed from a 5% strength solution of the rhamnolipid ester crude product. For careful separation, a fraction comprises 10 ml at a dropping rate of 15 ml/min and for a total volume of 200 ml of starting solution.

Analytical determination by means of HPLC was carried out on a 50*3.0 mm column Poroshell 120 C18 (2.7 μm) in 20 mM $NH_4$ formate in $H_2O$ and MeCN at 30° C. for 35 min.

Example 4: Non-Inventive Synthesis of Rhamnolipid Esters

The synthesis was carried out according to the specification of the publication Miao et al. European Journal of Lipid Science and Technology, 117, 2015; 156-1609.

For this purpose, di-rhamnolipid from Example 1 was reacted with ethanol and sulphuric acid at 0° C. as described in the literature. The verified yield was less than 5%. This is particularly attributed to, inter alia, the lack of coupling reagent.

Synthesis of long-chain rhamnolipid esters with C12 fatty alcohol at low temperatures was not possible, since these are in the solid state at 0° C., and therefore esterification is not possible; the conversion is 0%. On increasing the temperature, degradation of the reactant occurs and no rhamnolipid ester is formed; the conversion is 0%.

Example 5: Description of the Application Effects and the Formulation

In order to measure the influence of the specified structures on hair growth after shaving with shaving foam and cream formulations according to the invention, the following standardized application test was carried out with a trained panel of at least 33 panelists.

For this, the panelists were provided with shaving foam and cream formulations (see formulation 1-6) in anonymized pump dispensers for a home-use test. The panel was firstly divided into two subgroups a (men) and b (women). The shaving tests were carried out as a half-side test, where subgroup a assessed the influence on beard growth on the face and subgroup b assessed the influence on hair growth on the lower legs.

Group a: Shaving Foam for Sensitive Skin

| | Formulation 1 according to the invention | Formulation 2 | Formulation 5 |
|---|---|---|---|
| Water | 66.5 | 66.5 | 66.5 |
| Disodium Lauroamphodi-acetate; Sodium Lauryl sulphate, Hexylene Glycol | 18.6 | 20.0 | 18.6 |
| Disodium PEG-4 Cocamide MIPA sulphosuccinate | 10.0 | 10.0 | 10 |
| Cocamide MEA | 3.0 | 3.0 | 3.0 |
| Ricinolamidopropyltrimonium Methosulphate | 0.5 | 0.5 | 0.5 |
| Rhamnolipid ester from Example 3 | 1.4 | | |
| Rhamnolipid ethyl ester from Example 4 | | | 1.4 |
| Sodium Hydroxide (10% in water, to pH 8-8.5) | q.s | q.s | q.s |
| Preservative | q.s | q.s | q.s |

Group b: Shaving Foam for Delicate Skin

| | Formulation 3 according to the invention | Formulation 4 | Formulation 6 |
|---|---|---|---|
| Water | 76.5 | 76.5 | 76.5 |
| Coconut fatty acid | 1.4 | 1.4 | 1.4 |
| Monoethanolamine | 1.3 | 1.3 | 1.3 |
| Myristic acid | 3.5 | 3.5 | 3.5 |
| Sucrose Cocoate | 2.0 | 2.0 | 2.0 |
| Capryl/Capramidopropyl Betaine | 6.4 | 7.6 | 6.4 |
| Rhamnolipid ester from Example 3 | 1.2 | | |
| Rhamnolipid ethyl ester from Example 4 | | | 1.2 |
| Glycerol | 5.0 | 5.0 | 5.0 |
| Bis-PEG/PPG-20/20 Dimethicone | 1.7 | 1.7 | 1.7 |

-continued

|  | Formulation 3 according to the invention | Formulation 4 | Formulation 6 |
|---|---|---|---|
| Perfume | 0.3 | 0.3 | 0.3 |
| Hydroxypropyl Methyl-cellulose | 0.7 | 0.7 | 0.7 |
| Sodium Hydroxide (10% in water, to pH 8.5) | q.s | q.s | q.s |
| Preservative | q.s | q.s | q.s |

Group a

The face was cleaned and wetted in preparation for shaving. In each case, 1 pump stroke of the corresponding formulations was applied evenly per half of the face. After a contact time of 60+/−5 sec, the hair was removed using a Balea twin-blade disposable razor. The face was then washed with water and dried. The resulting skin feel was assessed once after 3 minutes and one further time after 8 hours+/−30 minutes and evaluated on a scale from 1 to 3.

1 silky, soft skin feel; smooth 2 less smooth, but no detectable beard stubble 3 detectable beard stubble; scratchy skin feel Group b The lower legs were cleaned and wetted in preparation for shaving. In each case, 3 pump strokes of the corresponding formulations were applied evenly per lower leg and, after a contact time of 60+/−5 sec, the hair was removed using a Balea twin-blade disposable razor. The legs were then washed with water and dried. The resulting skin feel was assessed once after 3 minutes and one further time after 24 hours and evaluated on a scale from 1 to 3.

1 silky, soft skin feel; smooth 2 less smooth, but no detectable hair 3 detectable hair; scratchy skin feel The Table below compares the results of the sensory assessment of the skin on the face (group a) and on the lower leg (group b) after shaving with formulations 1 and 3 according to the invention with the results of comparison formulations 2 and 4 and 5 and 6:

|  | Formulation | | | | | |
|---|---|---|---|---|---|---|
|  | 1 inv. | 2 | 3 inv. | 4 | 5 | 6 |
| Group a, after 3 minutes | 1.3 | 1.6 |  |  | 1.5 |  |
| Group a, after 8 hours | 1.7 | 2.5 |  |  | 2.3 |  |
| Group b, after 3 minutes |  |  | 1.2 | 1.4 |  | 1.6 |
| Group b, after 24 hours |  |  | 1.8 | 2.2 |  | 2.4 |

Surprisingly, it has been found that after using formulations 1 and 3 according to the invention, the smooth, silky-soft skin feel directly after shaving is retained for significantly longer than after using comparison formulations 2 and 4 and 5 and 6.

The invention claimed is:

1. A rhamnolipid ester of the general formula (I)

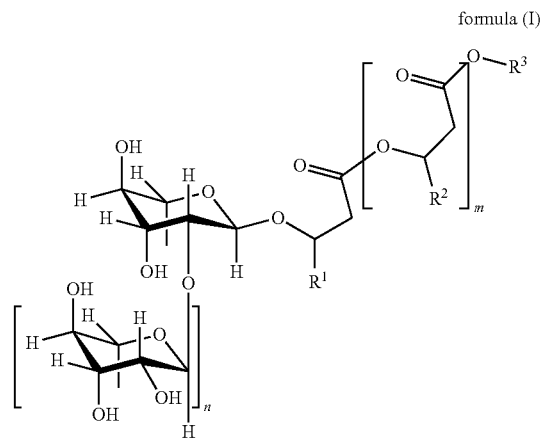

formula (I)

wherein m=2, 1 or 0 n=1 or 0

$R^1$=organic radical having 2 to 24 carbon atoms, $R^2$=independently of one another, identical or different, organic radical having 2 to 24 carbon atoms, and $R^3$ is selected from the group consisting of branched or linear alkyl radicals having 12 to 18 carbon atoms.

2. The rhamnolipid ester according to claim 1, wherein $R^3$ is selected from the group of the radicals $R^3$ derived from $OHR^3$=natural fatty alcohol.

3. The rhamnolipid ester according to claim 1, wherein the $R^3$ is selected from the group consisting of lauryl, myristyl, palmityl and stearyl radicals.

4. A process for the preparation of rhamnolipid ester comprising the process steps of
   A) providing at least one rhamnolipid,
   B) reacting the rhamnolipid with at least one coupling reagent,
   C) reacting the rhamnolipid activated by process step B) with an alcohol having 1 to 32 carbon atoms, and optionally
   D) purifying the rhamnolipid ester.

5. The process according to claim 4, wherein in process step B) the coupling reagent used is at least one selected from the group consisting of dicyclohexylcarbodiimide, diisopropylcarbodiimide, 1-(3-dimethylaminopropyl)-3-ethylcarbodiimide hydrochloride, N-cyclohexyl-N'-(2'-morpholinoethyl)carbodiimide metho-p-toluenesulphonate, N-benzyl-N'-3' dimethylaminopropylcarbodiimide hydrochloride, 1-ethyl-3-(3-dimethylaminopropyl)carbodiimide, N-ethylcarbodiimide hydrochloride and carbonyldiimidazole.

6. The process according to claim 4, wherein in process step C) at least one catalyst selected from the group consisting of N-ethyldiisopropylamine, trialkylamines, pyridine, 4-dimethylaminopyridine and hydroxybenzotriazole.

7. A cosmetic formulation, comprising at least one rhamnolipid ester according to claim 1.

8. A cosmetic application comprising the rhamnolipid ester according to a formulation according to claim 7.

9. A cosmetic application comprising the rhamnolipid ester according to a formulation according to claim 7 in formulations for inhibiting hair growth.

10. The rhamnolipid ester according to claim 1, wherein
m=1 or 0,
n=1
$R^1$=organic radical selected from the group consisting of pentenyl, heptenyl, nonenyl, undecenyl and tridecenyl and $(CH_2)_o$—$CH_3$ where o=1 to 23,
$R^2$=organic radical having 5 to 13 carbon atoms and selected from the group consisting of pentenyl, heptenyl, nonenyl, undecenyl and tridecenyl and $(CH_2)_o$—$CH_3$ where o=1 to 23.

11. The rhamnolipid ester according to claim 1, wherein
m=1 or 0,
n=1
$R^1$=organic radical selected from the group consisting of pentenyl, heptenyl, nonenyl, undecenyl and tridecenyl and $(CH_2)_o$—$CH_3$ where o=4 to 12,
$R^2$=organic radical having 5 to 13 carbon atoms and selected from the group consisting of pentenyl, heptenyl, nonenyl, undecenyl and tridecenyl and $(CH_2)_o$—$CH_3$ where o=4 to 12.

12. The rhamnolipid ester according to claim 1, wherein $R^3$ is selected from branched or linear alkyl radicals having 12 to 18 carbon atoms.

13. The process according to claim 4, wherein in process step B) the coupling reagent used is selected from the group consisting of dicyclohexylcarbodiimide and diisopropylcarbodiimide.

14. The process of claim 4, wherein in process step C) at least one catalyst is hydroxybenzotriazole.

15. A shaving application comprising the rhamnolipid ester according to a formulation according to claim 7.

16. The process according to claim 4, wherein for the rhamnolipid ester is the general formula (I)

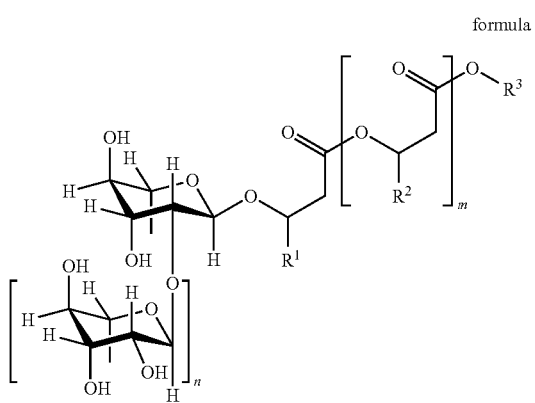

formula (I)

wherein
m=2, 1 or 0
n=1 or 0
$R^1$=organic radical having 2 to 24 carbon atoms,
$R^2$=independently of one another, identical or different, organic radical having 2 to 24 carbon atoms, and
$R^3$ is selected from the group consisting of branched or linear alkyl radicals having 12 to 18 carbon atoms.

17. The process of claim 4, wherein
m=1 or 0,
n=1
$R^1$=organic radical selected from the group consisting of pentenyl, heptenyl, nonenyl, undecenyl and tridecenyl and $(CH_2)_o$—$CH_3$ where o=1 to 23,
$R^2$=organic radical having 5 to 13 carbon atoms and selected from the group consisting of pentenyl, heptenyl, nonenyl, undecenyl and tridecenyl and $(CH_2)_o$—$CH_3$ where o=1 to 23.

18. The process of claim 4, wherein
m=1 or 0,
n=1
$R^1$=organic radical selected from the group consisting of pentenyl, heptenyl, nonenyl, undecenyl and tridecenyl and $(CH_2)_o$—$CH_3$ where o=4 to 12,
$R^2$=organic radical having 5 to 13 carbon atoms and selected from the group consisting of pentenyl, heptenyl, nonenyl, undecenyl and tridecenyl and $(CH_2)_o$—$CH_3$ where o=4 to 12.

19. The process of claim 4, wherein $R^3$ is selected from branched or linear alkyl radicals having 12 to 18 carbon atoms,
m=1 or 0,
n=1
$R^1$=organic radical selected from the group consisting of pentenyl, heptenyl, nonenyl, undecenyl and tridecenyl and $(CH_2)_o$—$CH_3$ where o=4 to 12,
$R^2$=organic radical having 5 to 13 carbon atoms and selected from the group consisting of pentenyl, heptenyl, nonenyl, undecenyl and tridecenyl and $(CH_2)_o$—$CH_3$ where o=1 to 23.

20. The process of claim 4, wherein the $R^3$ is selected from the group consisting of lauryl, myristyl, palmityl and stearyl radicals.

\* \* \* \* \*